United States Patent
Yoshikawa et al.

(10) Patent No.: US 10,619,027 B2
(45) Date of Patent: Apr. 14, 2020

(54) AGENT FOR SUPPRESSING ODORS OF POLYSULFIDE COMPOUNDS

(71) Applicant: KAO CORPORATION, Tokyo (JP)

(72) Inventors: Keiichi Yoshikawa, Saitama (JP); Naoko Saito, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 131 days.

(21) Appl. No.: 15/737,210

(22) PCT Filed: Jun. 16, 2016

(86) PCT No.: PCT/JP2016/067895
§ 371 (c)(1),
(2) Date: Dec. 15, 2017

(87) PCT Pub. No.: WO2016/204212
PCT Pub. Date: Dec. 22, 2016

(65) Prior Publication Data
US 2018/0186968 A1    Jul. 5, 2018

(30) Foreign Application Priority Data

Jun. 17, 2015 (JP) .................. 2015-121917
Jun. 10, 2016 (JP) .................. 2016-116226

(51) Int. Cl.
| | | |
|---|---|---|
| *C08K 5/06* | (2006.01) | |
| *C08K 5/07* | (2006.01) | |
| *C08K 5/01* | (2006.01) | |
| *C08K 5/101* | (2006.01) | |
| *A61L 9/01* | (2006.01) | |
| *A61K 31/473* | (2006.01) | |

(52) U.S. Cl.
CPC .................. *C08K 5/06* (2013.01); *A61L 9/01* (2013.01); *C08K 5/01* (2013.01); *C08K 5/07* (2013.01); *C08K 5/101* (2013.01); *A61K 31/473* (2013.01); *C08K 2201/007* (2013.01)

(58) Field of Classification Search
CPC .................................................. A61K 31/473
USPC .......................................................... 514/290
See application file for complete search history.

(56) References Cited

U.S. PATENT DOCUMENTS

| 5,559,271 A | 9/1996 | Shaw et al. |
|---|---|---|
| 2003/0088059 A1 | 5/2003 | Zozulya |
| 2008/0008665 A1 | 1/2008 | Ramji et al. |
| 2011/0024678 A1 | 2/2011 | Schmitt |
| 2013/0136713 A1 | 5/2013 | Terada et al. |
| 2013/0336910 A1 | 12/2013 | Chatelain et al. |

FOREIGN PATENT DOCUMENTS

| JP | 4-79961 A | 3/1992 |
|---|---|---|
| JP | 5-43454 A | 2/1993 |
| JP | 9-108261 A | 4/1997 |
| JP | 2002-253652 A | 9/2002 |
| JP | 2002-336337 A | 11/2002 |
| JP | 2003-190264 A | 7/2003 |
| JP | 2003-325648 A | 11/2003 |
| JP | 2004-18431 A | 1/2004 |
| JP | 2004-504010 A | 2/2004 |
| JP | 2006-182698 | 7/2006 |
| JP | 2006-206882 A | 8/2006 |
| JP | 2006-249092 A | 9/2006 |
| JP | 2008-173441 A | 7/2008 |
| JP | 2009-542694 A | 12/2009 |
| JP | 2010-4971 A | 1/2010 |
| JP | 2011-21195 A | 2/2011 |
| JP | 2012-50411 A | 3/2012 |
| JP | 2012-50781 A | 3/2012 |
| JP | 2012-65906 A | 4/2012 |
| JP | 2012-249614 A | 12/2012 |
| JP | 2014-33680 A | 2/2014 |
| JP | 2014-94968 A | 5/2014 |
| JP | 5575241 B2 | 8/2014 |
| WO | WO 01/68805 A2 | 9/2001 |
| WO | WO 2006/094704 A2 | 9/2006 |
| WO | WO 2013/154899 A2 | 10/2013 |

OTHER PUBLICATIONS

International Search Report dated Aug. 18, 2016, in PCT/JP2016/067895 filed Jun. 16, 2016.
Kazumi Osada et al., The Japanese Journal of Taste and Smell Research, vol. 18, No. 3, ISSN 1340-4806, (2011), with a partial English translation, 8 pages.

*Primary Examiner* — Kevin E Weddington
(74) *Attorney, Agent, or Firm* — Oblon, McClelland, Maier & Neustadt, L.L.P.

(57) ABSTRACT

Provided an agent for suppressing an odor of a polysulfide compound. This agent for suppressing an odor of a polysulfide compound comprises, as an active ingredient, at least one selected from the group consisting, butyl 2-methylbutanoate, α-terpinene, dipentene, cis-4-heptenal, 1,4-cineol, trimethylhexyl aldehyde, and (+)-limonene oxide, wherein the polysulfide compound is represented by the following formula (I): $R^1—[S]_n—R^2$ (I) (in the formula, $R^1$ and $R^2$ are the same or different, and each denote a linear-chain or branched-chain alkyl or alkenyl group having 1 to 6 carbon atoms, and n denotes an integer of 2 to 5).

15 Claims, 6 Drawing Sheets
Specification includes a Sequence Listing.

AGENT FOR SUPPRESSING ODORS OF POLYSULFIDE COMPOUNDS

FIELD OF THE INVENTION

The present invention relates to an agent for suppressing an odor of a polysulfide compound.

BACKGROUND OF INVENTION

Volatile sulfur compounds, which are generated from drain outlets or waste such as kitchen garbage, are malodorous components which give unpleasant feelings to people even at low concentration. These volatile sulfur compounds are generated through decomposition of sulfur-containing amino acid such as cysteine and methionine or a protein containing it in sewage, waste, or the like by the action of a metabolizing enzyme such as methionine lyase and cysteine lyase possessed by bacteria. Among volatile sulfur compounds responsible for unpleasent odors, for example, methylmercaptan is formed from methionine by the action of methionine lyase, and hydrogen sulfide is formed from cysteine by the action of cysteine lyase. Further, from methylmercaptan or hydrogen sulfide, polysulfide compounds including dimethyl disulfide and dimethyl trisulfide are enzymatically or oxidatively formed, and they are also responsible for malodors.

Patent Literature 1 discloses addition of a fragrance component as a deodorizer or an aromatic agent to a composition for washing, sterilization, anti-staining, deodorization for drain outlets or the like. Patent Literature 2 discloses that a particular fragrance component inhibits the action of an enzyme to form methylmercaptan from methionine or an enzyme to form hydrogen sulfide from cysteine to suppress malodors caused by volatile sulfur compounds generated from waste, drain outlets, etc.

Patent Literature 3 describes addition of an odor-masking agent containing at least one compound selected from the group consisting of a monoester, a diester, and/a triester, an alcohol, an aldehyde, a ketone, and a terpene to an oxide of organic sulfide (e.g., DMSO) for prevention of the odor of the oxide of organic sulfide.

Mammals including humans recognize a smell through the mechanism in which a smell molecule binds to an olfactory receptor (OR) on an olfactory sensory neuron (OSN) present in the olfactory epithelium in the upper part of the nasal cavity, and the response of the receptor thereto is transmitted to the central nerve system. For humans, it has been reported that approximately 400 olfactory receptors are present, and genes encoding them account for approximately 2% of the total genes of a human. In general, olfactory receptors and smell molecules are associated in many-to-many relationship. That is, an individual olfactory receptor receives a plurality of structurally similar smell molecules at different affinities, and an individual smell molecule is received by a plurality of olfactory receptors. In addition, it has been reported that a smell molecule which activates an olfactory receptor functions as an antagonist to inhibit the activation of another olfactory receptor. Combination of the responses of a plurality of olfactory receptors provides recognition of an individual smell.

Accordingly, the receptor response to one smell molecule may be inhibited by another smell molecule concomitantly present, which ultimately result in no smell recognizable. This mechanism is called olfactory receptor antagonism. In contrast to deodorization by addition of another smell of a perfume, an aromatic agent, or the like, the suppression of a smell through the receptor antagonism can specifically disable recognition of a particular malodor, and has advantage that unpleasant feelings due to a smell of an aromatic agent are not caused.

On the basis of the concept of the olfactory receptor antagonism, several methods for identifying malodor-suppressing substances by using the activity of an olfactory receptor as an indicator have been previous disclosed. For example, patent Literatures 4 and 5 disclose searching for substances which suppress malodors of hexanoic acid, skatole, etc., by using, as an indicator, the activity of an olfactory receptor specifically responsive the malodor substances. Patent Literature 6 discloses searching for substances which suppress sweat odor by using, as an indicator, the activity of an olfactory receptor responsive to a particular carboxylic acid(s). Patent Literature 7 discloses a method of identifying agents capable of regulating the function of a polypeptide encoding an olfactory receptor through measurement of the activity of the polypeptide in the presence of isovaleric acid or an equivalent thereof. Patent Literature 8 discloses a method of screening a library of chemical substances for compounds relating to olfactory causes through identification of compounds which specifically bind to a polypeptide encoding an olfactory receptor.

However, a technique to suppress malodors of the above-mentioned volatile sulfur compounds generated from waste, drain outlets, or the like on the basis of the odor receptor antagonism not been reported yet.

Patent Literature 1: JP-A-2006-206882
Patent Literature 2: JP-A-2010-004971
Patent Literature 3: JP-B-5575241
Patent Literature 4: JP-A-2012-050411
Patent Literature 5: JP-A-2012-249614
Patent Literature 6: US 2013/0336910 A1
Patent Literature 7: WO 2006/094704
Patent Literature 8: JP-A-2004-504010

SUMMARY OF THE INVENTION

In one aspect, the present invention provides an agent for suppressing an odor of a polysulfide compound, the agent comprising, as an active ingredient, at least one selected from the group consisting of butyl 2-methylbutanoate, α-terpinene, dipentene cis-4-heptenal, 1,4-cineol, trimethylhexyl aldehyde, and (+)-limonene oxide, wherein the polysulfide compound is represented by the following formula (I):

$$R^1\text{---}[S]_n\text{---}R^2 \qquad (I)$$

wherein $R^1$ and $R^2$ are the same or different, and each denote a linear-chain or branched-chain alkyl or alkenyl group having 1 to 6 carbon atoms, and n denotes an integer of 2 to 5.

DETAILED DESCRIPTION OF THE INVENTION

Various volatile sulfur compounds are generated from drain outlets or waste such as kitchen garbage in association with rot caused by bacteria, and cause malodors. One of main causal substances for such malodors is a polysulfide compound such as dimethyl disulfide and dimethyl trisulfide. Thus, control of odors of these polysulfide compounds is required.

The present inventors found that a substance which suppresses the response of the olfactory receptor OR4S2 specifically responsive to a polysulfide compound can suppress the odor of the polysulfide compound through the olfactory receptor antagonism.

The present invention enables selective deodorization of odors of polysulfide compounds including dimethyl disulfide and dimethyl trisulfide through the olfactory receptor antagonism.

In the present specification, the term "suppression of odor through the olfactory receptor antagonism" refers to a means in which an odor molecule of interest and an additional molecule are applied together to allow the additional molecule to inhibit the receptor response to the odor molecule of interest and eventually suppress odor recognized by an individual. Suppression of odor through the olfactory receptor antagonism is discriminated from a means in which odor of interest is hidden with an aromatic smell of a fragrance as deodorization with an aromatic agent, although the means is similar in that an additional molecule is used. One example of suppression of odor through the olfactory receptor antagonism is use of a substance inhibitory to the response of an olfactory receptor such as an antagonist (antagonistic agent). To a receptor for an odor molecule causing a particular odor, a substance inhibitory to the response of the receptor to the odor molecule is applied, and then the response of the receptor to the odor molecule is suppressed, and thus odor perceived by an individual can be ultimately suppressed.

In the present specification, the term "olfactory receptor polypeptide" term to an olfactory receptor or a polypeptide having a function comparable to an olfactory receptor, and the polypeptide having a function comparable to an olfactory receptor refers to a polypeptide which can be expressed on the cell membrane as an olfactory receptor, and is activated through binding with a smell molecule, and has a function to increase the intracellular cAMP level through conjugation with the intracellular Gαs on being activated followed by resulting activation of adenylate cyclase (Nat. Neurosci., 2004 5:263-278).

In the present specification, the identity of a nucleotide sequence and amino acid sequence is calculated by using a Lipman-Pearson method (Science, 1985, 227:1435-41). Specifically, calculation is performed by using a homology analysis (Search homology) program of the genetic information processing software Genetyx-Win (ver. 5.1.1; Software Development Co.) with "Unit size to compare (ktup)" set at 2.

In the present specification, the term "an identity of at least 80%" with respect to a nucleotide sequence and amino acid sequence refers to a identity of 80% or higher, preferably 85% or higher, more preferably 90% or higher, further preferably 95% or higher, furthermore preferably 98% or higher, still furthermore preferably 99% or higher.

The "polysulfide compound" the odor of which the present invention intends to suppress is a compound represented by the formula (I) below. Hereinafter, the targeted "polysulfide compound" is occasionally referred to as "the polysulfide compound of the formula or (I)", or simply as "the compound of the formula (I)".

$$R^1\text{—}[S]_n\text{—}R^2 \quad (I)$$

In the formula (I), $R^1$ and $R^2$ are the same or different, and each denote a linear-chain or branched-chain alkyl or alkenyl group having 1 to 6 carbon atoms. Examples of the linear-chain or branched-chain alkyl group having 1 to 6 carbon atoms include methyl, ethyl, propyl, isopropyl, butyl, isobutyl, sec-butyl, tert-butyl, pentyl, isopentyl, tert-pentyl, and hexyl. Examples of the linear-chain or branched-chain alkenyl group having 1 to 6 carbon atoms include vinyl, propenyl, allyl, butenyl, and methylbutenyl. Preferably, the $R^1$ and $R^2$ are the same or different, and are each a linear-chain or branched-chain alkyl or alkenyl group having 1 to 4 carbon atoms. Examples of the linear-chain or branched-chain alkyl or alkenyl group having 1 to 4 carbon atoms include methyl, ethyl, propyl, isopropyl, butyl, isobutyl, sec-butyl, tert-butyl, vinyl, propenyl, allyl, and butenyl. More preferably, the $R^1$ and $R^2$ are the same or different, and are each methyl, ethyl, propyl, or isopropyl. Still more preferably, the $R^1$ and $R^2$ are each methyl.

In the formula (I), n denotes an integer of 2 to 5, and preferably 2 or 3.

Preferably, the polysulfide compound of the formula (I) is a volatile substance having the structure represented by the formula (I). More preferred examples of the polysulfide compound of the formula (I) include dimethyl disulfide (DMDS) and dimethyl trisulfide (DMTS).

"Odors of polysulfide compounds" to be suppressed in the present invention are odors caused by the above-described polysulfide compound of the formula (I), and preferably odors caused by DMDS or DMTS. Representatively, "odors of polysulfide compounds" to be suppressed in the present invention may be malodors released from rotted kitchen garbage, sewage, or drain outlets.

As demonstrated later in Examples, the polysulfide compound of the formula (I) was revealed to be recognized primarily by OR4S2 (GI: 116517324 SEQ ID NO. 1) in olfactory receptors. Accordingly, it was expected that a substance which suppresses the response of the olfactory receptor OR4S2 can selectively suppress the odor of the polysulfide compound of the formula (I) through the olfactory receptor antagonism. On the basis of this idea, the present inventors searched for antagonist substances which suppress the response of OR4S2 to the compound of the formula (I). Consequently, it was found that the substances searched out actually have an odor-suppressing action for the polysulfide compound of the formula (I), and can be used for suppressing the odor of the polysulfide compound of the formula (I).

Thus, an OR4S2 antagonist (antagonistic agent) which suppresses the response of the olfactory receptor OR4S2 be used for suppressing the odor of the polysulfide compound of the formula (I). OR4S2 antagonists can change recognition of the odor of the polysulfide compound of the formula (I) by an individual by suppression of the response OR4S2 to the compound of the formula (I) through the olfactory receptor antagonism, and eventually suppress the odor of the compound of the formula (I).

Examples of OR4S2 antagonists include compounds listed in the following Table A.

[Table A]
Butyl 2-methylbutanoate (2-Methyl butyl n-butyrate)
α-Terpinene (p-Mentha-1,3-diene)
Dipentene
cis-4-Heptenal ((Z)-Hept-4-enal)
1,4-Cineol
Trimethylhexyl aldehyde (3,5,5-Trimethylhexanal)
(+)-Limonene oxide More specifically, the compounds listed in the above Table A are antagonists to OR4S2 or olfactory receptor polypeptides having a function comparable to OR4S2. In the present specification, an "olfactory receptor polypeptide having a function comparable to OR4S2" refers to an olfactory receptor polypeptide consisting of an amino acid sequence having an amino acid sequence identity of at least 80% as set forth in SEQ ID NO. 1, and having the responsiveness to the polysulfide compound of the formula (I), preferably responsive to DMDS and DMTS.

The compounds listed in Table A have been known as fragrance materials, and have not been known to have a function as an OR4S2 antagonist and a function to selectively suppress the odor of the compound of the formula (I).

The compounds listed in Table A are all commercially available. For example, they are available from Sigma-Aldrich Co., LLC. or Tokyo Chemical Industry Co., Ltd.

In one embodiment, the present invention provides an agent for suppressing the odor of the polysulfide compound of the formula (I), the agent comprising, as an active ingredient, an OR4S2 antagonist. In other words, the agent for suppressing odors of polysulfide compounds according to the present invention is a substance capable of functioning as an antagonist to OR4S2.

In one embodiment, the OR4S2 antagonist can be applied to any substance of which the odor of the polysulfide compound of the formula (I) is desired to be suppressed as an active ingredient for suppressing the odor of the compound of the formula (I), or can be used under any environment in which the odor of the compound of the formula (I) is desired to be suppressed.

In one embodiment, the OR4S2 antagonist can be added to a substance containing or possibly containing the polysulfide compound of the formula (I), as an active ingredient for suppressing the odor of the compound of the formula (I).

In another embodiment, the OR4S2 antagonist can be used for production of an agent for suppressing the odor of the polysulfide compound of the formula (I). In one embodiment, the agent for suppressing the odor of the compound of the formula (I) is a composition, and the OR4S2 antagonist is contained in the composition, as an active ingredient for suppressing the odor of the compound of the formula (I). Alternatively, the agent for suppressing the odor of the compound of the formula (I) may be essentially composed of the OR4S2 antagonist.

In a preferred embodiment, the OR4S2 antagonist to be used in the present invention is at least one selected from the group consisting of the compounds listed in Table A. For example, the OR4S2 antagonist to be used in the present invention is any one of the compounds listed in Table A, or combination of two or more thereof.

Further, the agent for suppressing the odor of the polysulfide compound of the formula (I) provided by the present invention may appropriately contain, together with the OR4S2 antagonist, an additional deodorizing component, an antiodor component or an aromatic component, or any component commonly added to a deodorizer or antiodor agent, in accordance with the purpose. Examples of such additional components include, but not limited to, a fragrance component described in Patent Literature 1 which can be contained in a composition for washing, sterilization, anti-staining, or deodorization for drain outlets or the like, and a fragrance described in Patent Literature 2 which ran contained in an agent for suppressing malodor generation for waste or drain outlets.

In a further embodiment, the present invention provides a method for suppressing the odor of the polysulfide compound of the formula (I), the method including a step of allowing the polysulfide compound of the formula (I) and an OR4S2 antagonist to coexist.

In one embodiment, the step of allowing to coexist in the method according to the present invention includes applying the OR4S2 antagonist to an individual in need of suppression of the odor of the polysulfide compound of the formula (I), preferably to an individual in need of suppression of the odor of the compound of the formula (I) through the olfactory receptor antagonism, in the presence of the compound of the formula (I). The antagonist applied acts on OR4S2 in the individual to suppress the response of the OR4S2 to the compound of the formula (I). As a result, the odor of the compound of the formula (I) is suppressed through the of olfactory receptor antagonism.

In another embodiment, the step of allowing to coexist in the method according the present invention includes applying the OR4S2 antagonist to an individual in need of suppression of the odor of the polysulfide compound of the formula (I), preferably to an individual in need of suppression of the odor of the compound of the formula (I) through the olfactory receptor antagonism, and exposing the individual to which the OR4S2 antagonist has been applied to the compound of the formula (I). The antagonist applied in advance acts on OR4S2 in the individual to suppress the response of the OR4S2 to the compound of the formula (I) to which the individual is to be exposed later. As a result, the odor of the compound of the formula (I) is suppressed through the olfactory receptor antagonism.

In a more detailed embodiment of the method according, to the present invention, the OR4S2 antagonist is carried by an individual in need of suppression of the odor of the polysulfide compound of the formula (I). Thereby, the OR4S2 antagonist is applied to the individual. Even when the individual to which the OR4S2 antagonist has been applied is exposed to the compound of the formula (i), OR4S2 exhibits a low response to the polysulfide compound, and as a result the odor of the compound of the formula (I) is suppressed.

In another detained embodiment, the OR4S2 antagonist is disposed in an environment in which the polysulfide compound of the formula (I) is present or possibly present. Thereby, the OR4S2 antagonist is applied to an individual in need of suppression of the odor of the polysulfide compound of the formula (I) in the environment. Even when the individual to which the OR4S2 antagonist has been applied is exposed to the compound of the formula (I) OR4S2 exhibits a low response to the polysulfide compound, and as a result the odor of the compound of the formula (I) is suppressed.

In still another detailed embodiment, the OR4S2 antagonist is added to a substance containing or possibly containing the polysulfide compound of the formula (I). Preferably, a composition of a substance containing or possibly containing the polysulfide compound of the formula (I) and the OR4S2 antagonist is prepared, and the composition is applied to an individual in need of suppression of the odor of the compound of the formula (I). Even when the composition releases the odor of the compound of the formula (I), the OR4S2 antagonist suppresses the response of OR4S2, and as a result the odor of the compound the formula (I) is suppressed.

In a preferred embodiment, the OR4S2 antagonist to be applied to the method according to the present invention is at least one selected from the group consisting of the compounds listed in Table A. In another preferred embodiment, a composition containing the above-described at least one selected from the group consisting of the compounds listed in Table A as an active ingredient is applied as the OR4S2 antagonist.

In the method according to the present invention, the individual (subject) may be any mammal without any limitation. However, the individual is preferably a human. More specific examples of individuals in need of suppression of the odor of the polysulfide compound of the formula (I) in the method according to the present invention include persons handling kitchen garbage at home or at work, persons involved in garbage cleaning or garbage collection, and persons involved in inspection, cleaning or construction of drainpipes or sewage treatment facilities.

As exemplary embodiments of the present invention, the following substances, production methods, applications, and methods are disclosed herein. However, the present invention is never limited to these embodiments.

[1] An agent for suppressing an odor of a polysulfide compound, the agent comprising an olfactory receptor OR4S2 antagonist as an active ingredient.
[2] Use of an olfactory receptor OR4S2 antagonist for suppressing an odor of a polysulfide compound.
[3] Use of an olfactory receptor OR4S2 antagonist for producing an agent for suppressing odor of a polysulfide compound.
[4] A method for suppressing an odor of a Polysulfide compound, the method including applying an olfactory receptor OR4S2 antagonist to an individual in need of suppression of an odor of a polysulfide compound.
[5] In any one of the above [1] to [4], the polysulfide compound is preferably a compound represented by the following formula (I):

wherein $R^1$ and $R^2$ are the same or different, and each denote a linear-chain ranched-chain alkyl or alkenyl group having 1 to 6 carbon atoms, and n denotes an integer of 2 to 5.

[6] In the above [5],
preferably, the $R^1$ and $R^2$ are the same or different, and are each a linear-chain or branched-chain alkyl or alkenyl group having 1 to 4 carbon atoms,
more preferably, the $R^1$ and $R^2$ are the same or different, and are each methyl, ethyl, propyl, or isopropyl, and
further preferably, the $R^1$ and $R^2$ are each methyl.
[7] In any one of the above [5] or [6], the n is preferably 2 or 3.
[8] In any one of the above [1] to [7], the polysulfide compound preferably dimethyl disulfide or dimethyl trisulfide.
[9] In any one of the above [1] to [8], the odor of the polysulfide compound is preferably malodor released from rotted kitchen garbage, sewage, or drain outlets.
[10] In any one of the above [1] to [9], the OR4S2 antagonist is preferably at least one selected from the group consisting of butyl 2-methylbutanoate, α-terpinene, dipentene, cis-4-heptenal, 1,4-cineol, trimethylhexyl aldehyde, and (+)-limonene oxide.
[11] An antagonistic agent to OR4S2 or olfactory receptor polypeptides having a function comparable to OR4S2, the antagonistic agent comprising, as an active ingredient, at least one selected from the group consisting of butyl 2-methylbutanoate, α-terpinene, dipentene, cis-4-heptenal, 1,4-cineol, trimethylhexyl aldehyde, and (+)-limonene oxide.
[12] Use of at least one selected from the group consisting of butyl 2-methylbutanoate, α-terpinene, dipentene, cis-4-heptenal, 1,4-cineol, trimethylhexyl aldehyde, and (+)-limonene as an antagonist to OR4S2 or olfactory receptor polypeptides having a function comparable to OR4S2.
[13] In the above [11] or [12],
preferably, the OR4S2 s an olfactory receptor polypeptide consisting of an amino acid sequence as set forth in SEQ ID NO 1, and
preferably, each of the olfactory receptor polypeptides having a function comparable to OR4S2 is an olfactory receptor polypeptide consisting of an amino acid sequence having an amino acid sequence identity of at least 80% as set forth in SEQ ID NO. 1, and is responsive to the polysulfide compound represented by the following formula (I);

wherein $R^1$ and $R^2$ are the same or different, and each denote a linear-chain or branched-chain alkyl or alkenyl group having 1 to 6 carbon atoms, and a denotes an integer of 2 to 5.

[14] In the above [13],
preferably, the $R^1$ and $R^2$ are the same or different, and are each a linear-chain or branched-chain alkyl or alkenyl group having 1 to 4 carbon atoms,
more preferably the $R^1$ and $R^2$ are the same or different, and are each methyl, ethyl, propyl, or isopropyl, and
further preferably, the 1 and $R^2$ are each methyl.
[15] In the above [13] or [14], the n is preferably 2 or 3.
[16] In any one of the above [13] to [15], the polysulfide compound is preferably dimethyl disulfide or dimethyl trisulfide.

EXAMPLES

Hereinafter, the present invention will be more specifically described with reference to Examples.

Odor compounds and test substances use in Examples are listed in the following Table 1.

TABLE 1

| | Cas No. | Name of provider |
|---|---|---|
| Polysulfide compound | | |
| Dimethyl disulfide (DMDS) | 624-92-0 | SIGMA-ALDRICH CO., LCC. |
| Dimethyl trisulfide (DMTS) | 3658-80-8 | SIGMA-ALDRICH CO., LCC. |
| Sulfur compound | Cas No. | Name of provider |
| Methylmercaptan | 5188-07-8 | Tokyo Chemical Industry Co., Ltd. |
| Test substance | | |
| Trimethylhexyl aldehyde (THA; or 3,5,5-Trimethylhexanal) | 5435-64-3 | SIGMA-ALDRICH CO., LCC. |
| Cis-4-Heptenal (or (Z)-Hept-4-enal) | 6728-31-0 | SIGMA-ALDRICH CO., LCC. |
| 1,4-Cineole | 470-67-7 | SIGMA-ALDRICH CO., LCC. |
| Limonene oxide ((+)-Limonene oxide, mixture of cis and trans) | 1195-92-2 | SIGMA-ALDRICH CO., LCC. |
| 2-Methyl butyl n-butyrate (or Butyl 2-methylbutanoate) | 15706-73-7 | SIGMA-ALDRICH CO., LCC. |
| α-Terpinene (or p-Mentha-1,3-diene) | 99-86-5 | SIGMA-ALDRICH CO., LCC. |
| Dipentene | 138-86-3 | SIGMA-ALDRICH CO., LCC. |

Example 1: Identification of Olfactory Receptor Responsive to Polysulfide Compound (1) Cloning of Human Olfactory Receptor Gene A human olfactory receptor cloned using the PCR method with human genomic DNA female (G1521: Promega Corporation) as a template on the basis of sequence information registered in GenBank. Each gene amplified through the PCR method was incorporated into a pENTR vector (Invitrogen) in accordance with the manual, and recombined, by utilizing the NotI and AscI sites present in the pENTR vector, with a pME18S vector at the NotI and AscI sites produced in the downstream of the Flag-Rho tag sequence of the pME18S vector.

(2) Preparation of pME18S-human RTP1S Vector

A vector expressing receptor-transporting protein (RTP), a protein which promotes the expression of an olfactory receptor polypeptide on the cell membrane, was prepared. Specifically, a gene encoding human RTP1S (GI: 50234917) was incorporated into a pME18S vector at the EcoRI and XhoI sites thereof.

(3) Preparation of Olfactory Receptor-expressing Cells

HEK293 cells expressing any one of human olfactory receptors were produced. A reaction solution with a composition shown in Table 2 was prepared and left to stand in a clean bench for 15 minutes, and then added to each well of a 96-well plate (BD Biosciences). Subsequently, 90 μL of HEK293 cells ($3 \times 10^5$ cells/cm$^2$) was seeded in each well, and cultured in an incubator retained at 37° C. and 5% $CO_2$ for 24 hours. As a control, cells with conditions for no expression of an olfactory receptor (Mock) were prepared and used in an experiment.

TABLE 2

| DMEM (Nacalai) | 10 μL |
|---|---|
| human olfactory receptor gene | 0.075 μg |

TABLE 2-continued

| (incorporated in pME18S vector with addition of Flag-Rho tag at N-terminal) | |
|---|---|
| pGL4.29 (fluc2P-CRE-hygro, Promega Corporation) | 0.03 μg |
| pGL4.75 (hRluc-CMV, Promega Corporation) | 0.03 μg |
| pME18S-human RTP1S vector | 0.03 μg |
| lipofectamine 2000 (Invitrogen) | 0.4 μL |

(4) Luciferase Assay

An olfactory receptor expressed on HEK293 cells increases the intracellular cAMP level through conjugation with the intracellular Gαs followed by resulting activation of adenylate cyclase. For smell response measurement in this study, luciferase reporter gene assay was used in which increase of the intracellular cAMP level is monitored as an emission value derived from a firefly luciferase gene (fluc2P-CRE-hygro). Transgenesis was simultaneously performed by using a product with a sea pansy luciferase gene fused to the downstream of the CMV promoter (hRluc-CMV), and the resultant was used as an internal standard to correct errors of transgenesis efficiency and the number of cells.

The medium was removed from the culture prepared in the above (3), and 75 μL of a solution containing a polysulfide compound prepared with DMEM (NACALAI TESQUE, INC.) was added. The polysulfide compound was 100 μM of dimethyl disulfide (DMDS) or dimethyl trisulfide (DMTS). The cells were cultured in a $CO_2$ incubator for 3 hours to allow the luciferase gene to be sufficiently expressed in the cells. Measurement of the activity of luciferase was performed by using a Dual-Glo™ luciferase assay system (Promega Corporation) in accordance with an operation manual of the product. For each stimulus condition, the value fLuc/hRluc was calculated by dividing the emission value derived from sea pansy luciferase. The value fLuc/hRluc derived from firefly luciferase and induced by a stimulus of a polysulfide compound was divided by the value fLuc/hRluc for cells without a stimulus of a polysulfide compound to calculate a fold increase, and the fold increase was used as an indicator of intensity of response.

(5) Results

Figure 1:
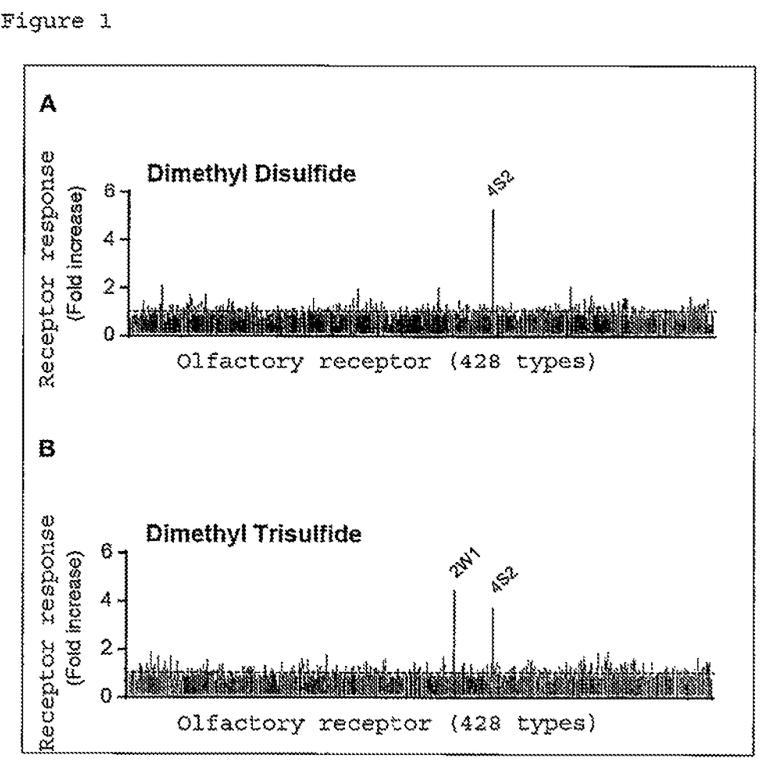
FIG. 1 shows the response of olfactory receptors to each sulfide compound. The horizontal axis represents individual olfactory receptors, and the vertical axis represents the intensity of response. The data are each an average value from three independent experiments. A: response to dimethyl disulfide, B: response to dimethyl sulfide.
Figure 2:
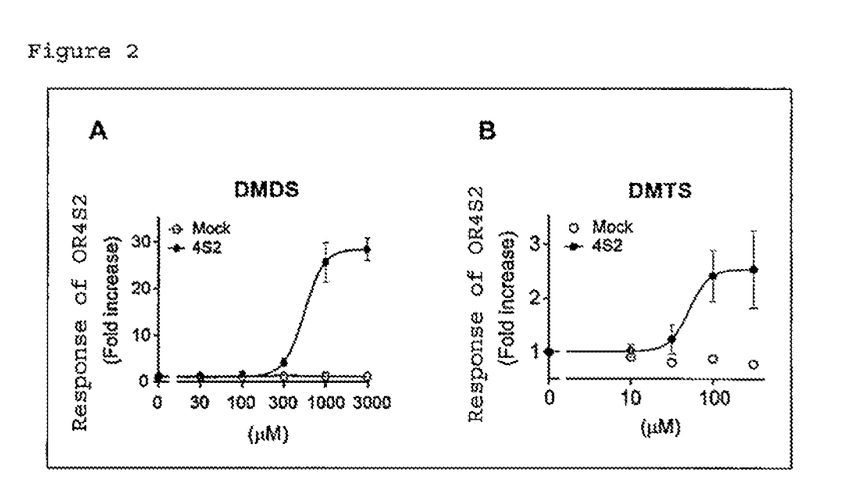
FIG. 2 shows the response of the olfactory receptor OR4S2 to sulfide pounds at different concentrations. A: response to dimethyl disulfide (DMDS), B: response to dimethyl trisulfide (DMTS). For each of the data, n=3, error bar=±SE.
Figure 3:
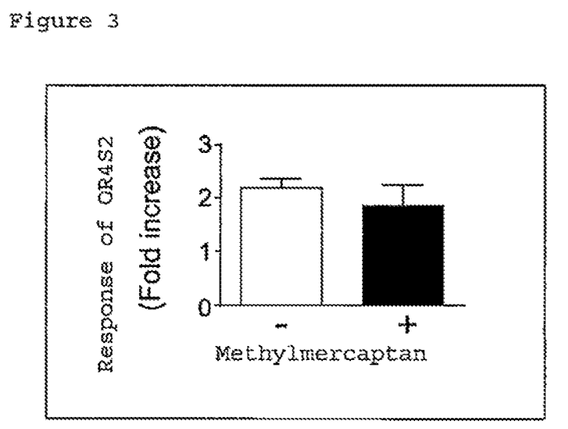
FIG. 3 shows the response of OR4S2 to methylmercaptan. +: with test substance (3 mM), −: without test substance, n=3, error bar=SD.

The response to DMDS or DMTS was measured for 428 olfactory receptors, and the results revealed that the olfactory receptor OR4S2 exhibits a specific response to both of DMDS and DMTS (FIG. 1). The response of OR4S2 to DMDS and DMTS was in a concentration-dependent manner (FIG. 2). On the other hand, OR4S2 did not respond to 3 mm of methylmercaptan FIG. 3), which is also a volatile sulfur compound. Therefore, OR4S2 is a polysulfide compound receptor responsive to polysulfide compounds. Further, OR4S2 is a novel polysulfide compound receptor which has not been found to respond to polysulfide compounds.

Example 2: Searching for OR452: =Antagonist

By using the same procedure as in Example 1 (1) to (3), HEK293 cells expressing OR4S2 (SEQ ID NO: 1) were prepared. The response of the olfactory receptor to DMDS (the value fLuc/hRluc) was measured in the presence and absence of a test substance by using luciferase reporter gene assay in accordance with the procedure in Example 1 (4). The value fLuc/hRluc induced by a stimulus of single DMDS, (X), the value fLuc/hRluc for cells without a stimulus of DMDS, (Y), and the value fLuc/hRluc induced by a co-stimulus of DMDS and a test substance, (Z), were determined, and the intensity of the response (Response (%)) of the receptor to DMDS in the presence of a test substance was determined by using the following formula.

Response (%)=(Z−Y)/(X−Y)×100

The experiment s performed independently three times, and the average value of the experiments was determined. The concentration of DMDS to be added to a culture was set a 1 mM, and the concentration of a test substance to be added was changed in the range of 0 to 3000 μM.

For the response to DMTS, the value fLuc/hRluc to a stimulus of single DMTS, (X'), was divided by the value fLuc/hRluc for cells without a stimulus of DMTS, (Y), and the calculated value, (X'/Y), was calculated as a value of the response to DMTS Fold increase). To compare the effect of a test substance on the response to DMTS, the value fLuc/hRluc induced by a co-stimulus of DMTS and a test substance, (Z'), was similarly divided by the value fLuc/hRluc for cells without a stimulus, (Y), to calculate (Z'/Y) as Fold increase. The experiment was performed independently three times, and the average value of the experiments was determined. The concentration of DMTS to be added to a culture was set at 300 μM, and the concentration of a test substance to be added set at 100 μM.

Figure 4:
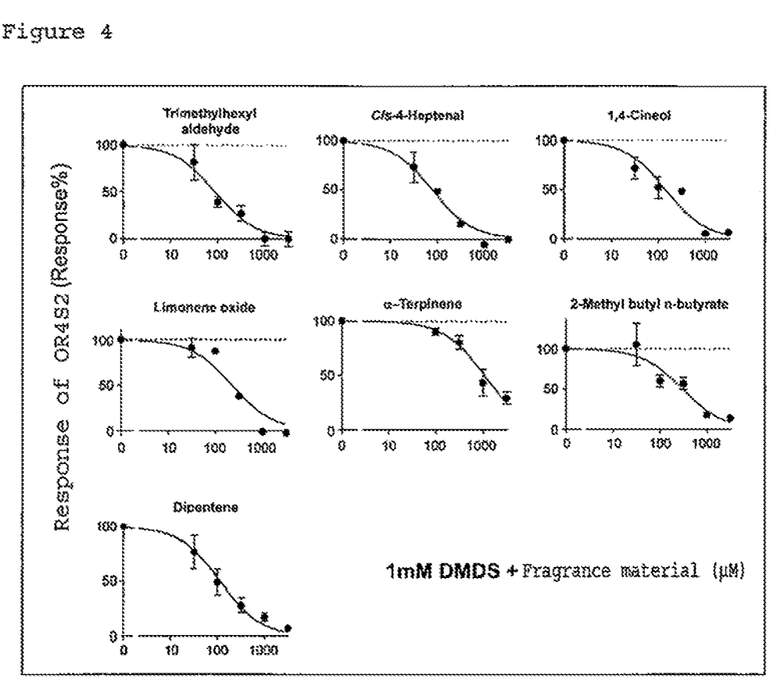
FIG. 4 shows the effect of suppressing the response of the olfactory receptor OR4S2 to dimethyl disulfide (DMDS) with different test substances. The horizontal axis represents the concentration of a test substance, and the vertical axis represents response (Response %) of OR4S2 to DMDS. n=3, error bar=±SE.
Figure 5:
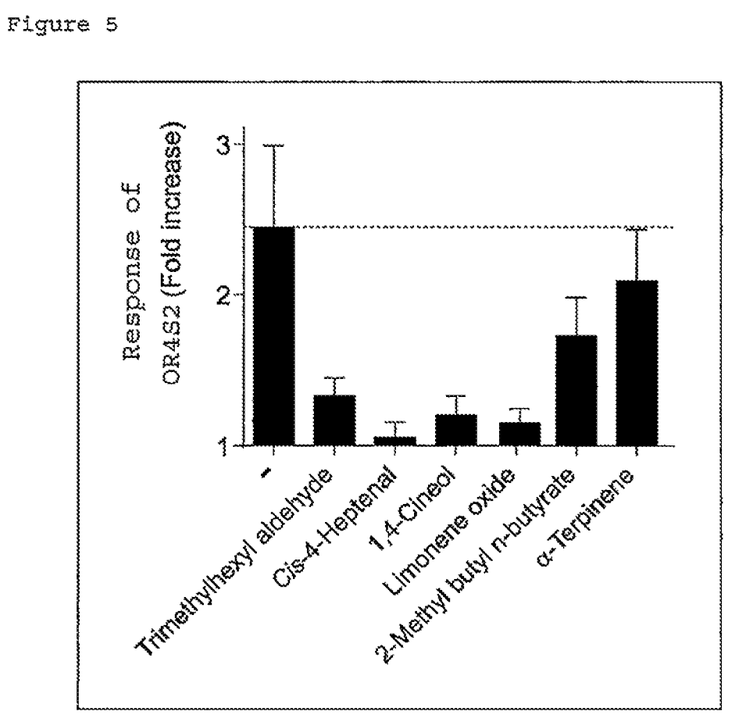
FIG. 5 shows the effect of suppressing the response of the olfactory receptor OR4S2 to dimethyl trisulfide (DMTS) with different test substances. The vertical axis represents the response (Fold increase). The OR4S2 to DMTS in the presence of a test substance. −: without test substance. n=3, error bar=SE.

The results are shown in FIGS. 4 and 5. Trimethylhexyl aldehyde (THA), cis-4-heptenal, 1,4-cineol, (+)-limonene oxide, α-terpinene, butyl 2-methylbutanoate, and dipentene all suppressed the response of OR4S2 to DMDS in a concentration-dependent manner, and thus these seven compounds were revealed to be OR4S2 antagonists. In addition, trimethylhexyl aldehyde (THA), cis-4-heptenal, 4-cineol, (+)-limonene oxide, α-terpinene, and butyl 2-methylbutanoate all suppressed the response of OR4S2 to DMTS.

Example 3: Ability of OR4S2 Antagonists to Suppress Odors of Polysulfide Compounds The odor-suppressing effect of each of trimethylhexyl aldehyde (THA), cis-4-heptenal, and 1,4-cineol, as the OR4S2 antagonists identified in Example 2, for polysulfide compounds was checked in a sensory test.

For each of DMDS, THA, cis-4-heptenal, and 1,4-cineol, a 0.1% (v/v) solution in mineral oil was prepared. For DMTS, a 0.01% (v/v) solution in mineral oil was prepared.

Two cotton balls were put in 20 mL glass bottle (Maruemu Corporation, No. 6), and one cotton ball was impregnated with 30 μL of the DMDS or DMTS solution, and the other cotton ball was impregnated with 30 μL of a solution of one of the three OR4S2 antagonists. The glass bottle containing the cotton balls was covered with a lid, and left to stand at 37° C. for 1 hour, and thereafter used as a test sample for a sensory test. Glass bottles containing only cotton ball impregnated with the DMDS or DMTS solution were prepared as reference samples, and a glass bottle containing only cotton ball impregnated with mineral oil (Vehicle) was prepared as a control sample.

A sensory test was performed in a single-blinded mode with 10 evaluators for DMDS and 11 evaluators for DMTS. The test was initiated after two o'clock pm, which was 1.5 hours or longer after a meal. To prevent diffusion of a smell, the test was performed essentially under a fume hood. To eliminate the influence of adaptation to odors of polysulfide compounds, the evaluators were appropriately checked for the intensity of recognition to the odor of DMDS or DMTS in the test, and rested as necessary. The evaluators were separated into two groups, and one group evaluated the odor-suppressing effect for DMDS or DMTS with respect to THA, cis-4-heptenal, and 1,4-cineol, in the presented, and the other group evaluated in with respect to 1,4-cineol, cis-4-heptenal, and THA, in the order presented. Each test sample was replaced with another one after evaluation by each of three evaluators.

In evaluation of odors of test samples, the following criteria in five grades were set for each evaluator; "odor of DMDS (or DMTS) was 1: unidentifiable, 2: perceivable, 3: easily identifiable, 4: strong, 5: intolerably strong", and the evaluators rated the odor intensity of DMDS (or DMTS) for each test sample in nine grades from 1.0 to 5.0 at an interval of 0.5, where the odor intensity of single DMDS (or DMTS) was assumed as 3. The average value of the evaluation results by the evaluators was determined.

Figure 6:
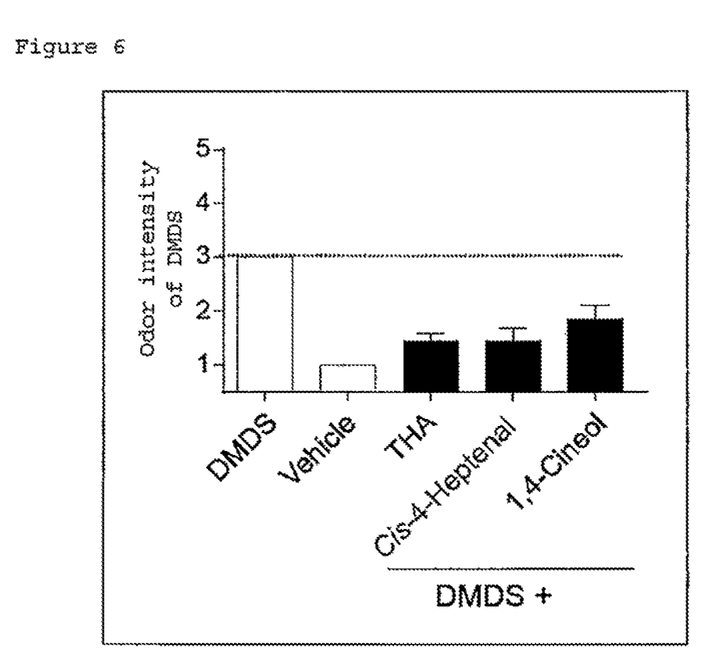
FIG. 6 shows results of sensory evaluation of the odor-suppressing effect of test substances for DMDS. DMDS=single DMDS, Vehicle=single mineral oil, n=10, error bar=SE.
Figure 7:
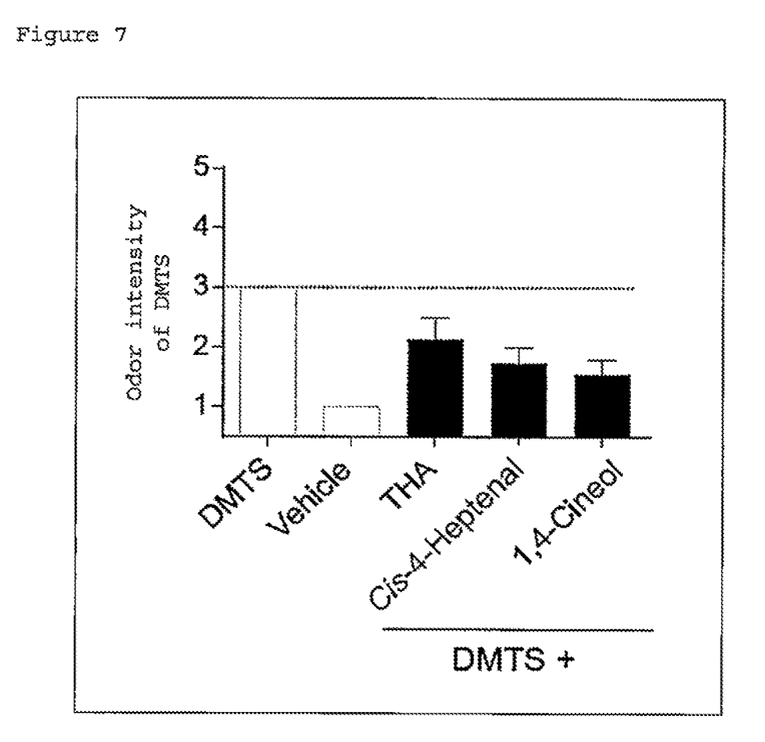
FIG. 7 shows results of sensory evaluation of the odor-suppressing effect of test substances for DMTS, DMTS=single DMTS, vehicle=mineral oil, n=11, error bar=SE.

The results of the sensory test are shown in FIG. 6 and FIG. 7. THA, cis-4-heptenal, and 1,4-cineol, each as an OR4S2 antagonist, all suppressed the odor intensity of DMDS and DMTS. The above-described results revealed that the OR4S2 antagonists suppress odors of polysulfide compounds including DMDS and DMTS.

The invention claimed is:

1. A method for suppressing an odor of a polysulfide compound, the method comprising applying at least one compound selected from the group consisting of butyl 2-methylbutanoate, dipentene, cis-4-heptenal, 1,4-cineol, trimethylhexyl aldehyde, and (+)-limonene oxide to an individual in need of suppression of an odor of a polysulfide compound, wherein the polysulfide compound is represented by the following formula (I):

$$R^1-[S]_n-R^2 \qquad (I)$$

wherein $R^1$ and $R^2$ are the same or different, and each denote a linear-chain or branched-chain alkyl or alkenyl group having 1 to 6 carbon atoms, and n denotes an integer of 2 to 5.

2. The method for suppressing an odor of a polysulfide compound according to claim 1, wherein the $R^1$ and $R^2$ of the polysulfide compound are the same or different, and are each a linear-chain or branched-chain alkyl or alkenyl group having 1 to 4 carbon atoms, and n is 2 or 3.

3. The method for suppressing an odor of a polysulfide compound according to claim 1, wherein the polysulfide compound is dimethyl disulfide or dimethyl trisulfide.

4. The method for suppressing an odor of a polysulfide compound according to claim 1, comprising applying butyl 2-methylbutanoate to an individual in need of suppression of an odor of a polysulfide compound.

5. The method for suppressing an odor of a polysulfide compound according to claim 1, comprising applying dipentene to an individual in need of suppression of an odor of a polysulfide compound.

6. The method for suppressing an odor of a polysulfide compound according to claim 1, comprising applying cis-4-heptenal to an individual in need of suppression of an odor of a polysulfide compound.

7. The method for suppressing an odor of a polysulfide compound according to claim 1, comprising applying 1,4-cineol to an individual in need of suppression of an odor of a polysulfide compound.

8. The method for suppressing an odor of a polysulfide compound according to claim 1, comprising applying trimethylhexyl aldehyde to an individual in need of suppression of an odor of a polysulfide compound.

9. The method for suppressing an odor of a polysulfide compound according to claim 1, comprising applying (+)-limonene oxide to an individual in need of suppression of an odor of a polysulfide compound.

10. The method for suppressing an odor of a polysulfide compound according to claim 3, comprising applying butyl 2-methylbutanoate to an individual in need of suppression of an odor of a polysulfide compound.

11. The method for suppressing an odor of a polysulfide compound according to claim 3, comprising applying dipentene to an individual in need of suppression of an odor of a polysulfide compound.

12. The method for suppressing an odor of a polysulfide compound according to claim 3, comprising applying cis-4-heptenal to an individual in need of suppression of an odor of a polysulfide compound.

13. The method for suppressing an odor of a polysulfide compound according to claim 3, comprising applying 1,4-cineol to an individual in need of suppression of an odor of a polysulfide compound.

14. The method for suppressing an odor of a polysulfide compound according to claim 3, comprising applying trimethylhexyl aldehyde to an individual in need of suppression of an odor of a polysulfide compound.

15. The method for suppressing an odor of a polysulfide compound according to claim 3, comprising applying (+)-limonene oxide to an individual in need of suppression of an odor of a polysulfide compound.

* * * * *

SEQUENCE LISTING

```
<160> NUMBER OF SEQ ID NOS: 1

<210> SEQ ID NO 1
<211> LENGTH: 311
<212> TYPE: PRT
<213> ORGANISM: Homo sapiens
<220> FEATURE:
<223> OTHER INFORMATION: Human OR4S2

<400> SEQUENCE: 1

Met Glu Lys Ile Asn Asn Val Thr Glu Phe Ile Phe Trp Gly Leu Ser
1               5                   10                  15

Gln Ser Pro Glu Ile Glu Lys Val Cys Phe Val Val Phe Ser Phe Phe
            20                  25                  30

Tyr Ile Ile Ile Leu Leu Gly Asn Leu Leu Ile Met Leu Thr Val Cys
        35                  40                  45

Leu Ser Asn Leu Phe Lys Ser Pro Met Tyr Phe Phe Leu Ser Phe Leu
    50                  55                  60
```

```
Ser Phe Val Asp Ile Cys Tyr Ser Ser Val Thr Ala Pro Lys Met Ile
 65              70              75              80
Val Asp Leu Leu Ala Lys Asp Lys Thr Ile Ser Tyr Val Gly Cys Met
                85              90              95
Leu Gln Leu Phe Gly Val His Phe Phe Gly Cys Thr Glu Ile Phe Ile
            100             105             110
Leu Thr Val Met Ala Tyr Asp Arg Tyr Val Ala Ile Cys Lys Pro Leu
            115             120             125
His Tyr Met Thr Ile Met Asn Arg Glu Thr Cys Asn Lys Met Leu Leu
130             135             140
Gly Thr Trp Val Gly Gly Phe Leu His Ser Ile Ile Gln Val Ala Leu
145             150             155             160
Val Val Gln Leu Pro Phe Cys Gly Pro Asn Glu Ile Asp His Tyr Phe
            165             170             175
Cys Asp Val His Pro Val Leu Lys Leu Ala Cys Thr Glu Thr Tyr Ile
            180             185             190
Val Gly Val Val Val Thr Ala Asn Ser Gly Thr Ile Ala Leu Gly Ser
        195             200             205
Phe Val Ile Leu Leu Ile Ser Tyr Ser Ile Ile Leu Val Ser Leu Arg
        210             215             220
Lys Gln Ser Ala Glu Gly Arg Arg Lys Ala Leu Ser Thr Cys Gly Ser
225             230             235             240
His Ile Ala Met Val Val Ile Phe Phe Gly Pro Cys Thr Phe Met Tyr
                245             250             255
Met Arg Pro Asp Thr Thr Phe Ser Glu Asp Lys Met Val Ala Val Phe
            260             265             270
Tyr Thr Ile Ile Thr Pro Met Leu Asn Pro Leu Ile Tyr Thr Leu Arg
            275             280             285
Asn Ala Glu Val Lys Asn Ala Met Lys Lys Leu Trp Gly Arg Asn Val
290             295             300
Phe Leu Glu Ala Lys Gly Lys
305             310
```